US008093396B2

(12) United States Patent
Przytulinska et al.

(10) Patent No.: US 8,093,396 B2
(45) Date of Patent: Jan. 10, 2012

(54) BENZTHIAZOLE INHIBITORS OF POLY(ADP-RIBOSE)POLYMERASE

(75) Inventors: Magdalena K. Przytulinska, Chicago, IL (US); Thomas D. Penning, Elmhurst, IL (US); Yunsong Tong, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 12/689,290

(22) Filed: Jan. 19, 2010

(65) Prior Publication Data
US 2010/0183743 A1 Jul. 22, 2010

Related U.S. Application Data

(60) Provisional application No. 61/145,640, filed on Jan. 19, 2009.

(51) Int. Cl.
C07D 277/62 (2006.01)
A61K 31/425 (2006.01)
(52) U.S. Cl. ........................................ 548/180; 514/367
(58) Field of Classification Search .................. None
See application file for complete search history.

(56) References Cited

U.S. PATENT DOCUMENTS

| | | | |
|---|---|---|---|
| 3,864,385 A | 2/1975 | Feit et al. |
| 4,093,726 A | 6/1978 | Winn et al. |
| 6,372,736 B1 | 4/2002 | Kemp et al. |
| 6,448,271 B1 | 9/2002 | Lubisch et al. |
| 6,509,365 B1 | 1/2003 | Lubisch et al. |
| 6,696,437 B1 | 2/2004 | Lubisch et al. |
| 6,737,421 B1 | 5/2004 | Lubish et al. |
| 7,166,292 B2 | 1/2007 | Isele et al. |
| RE39,608 E | 5/2007 | Lubisch et |
| 2003/0100582 A1 | 5/2003 | Sircar et al. |
| 2005/0159427 A1 | 7/2005 | Bruncko et al. |
| 2006/0229289 A1 | 10/2006 | Zhu et al. |
| 2006/0229351 A1 | 10/2006 | Zhu et al. |
| 2007/0112047 A1 | 5/2007 | Penning et al. |
| 2007/0179136 A1 | 8/2007 | Penning et al. |
| 2007/0208066 A1 | 9/2007 | Barlaam et al. |
| 2007/0259937 A1 | 11/2007 | Giranda et al. |
| 2008/0108659 A1 | 5/2008 | Gandhi et al. |
| 2009/0030016 A1 | 1/2009 | Gandhi et al. |

FOREIGN PATENT DOCUMENTS

| | | |
|---|---|---|
| DE | 3522230 A1 | 1/1987 |
| DE | 3830060 A1 | 3/1990 |
| DE | 19916460 A1 | 10/2000 |
| DE | 10021468 A1 | 11/2001 |
| GB | 1354554 A | 5/1974 |
| WO | WO9704771 A1 | 2/1997 |
| WO | WO9839343 A1 | 9/1998 |
| WO | WO0026192 A1 | 5/2000 |
| WO | WO0032579 A1 | 6/2000 |
| WO | WO0121615 A1 | 3/2001 |
| WO | WO0121634 A1 | 3/2001 |
| WO | WO0182877 A2 | 11/2001 |
| WO | WO02051821 A1 | 7/2002 |
| WO | WO02068407 A1 | 9/2002 |
| WO | WO03002698 A2 | 1/2003 |
| WO | WO03020698 A2 | 3/2003 |
| WO | WO03050095 A1 | 6/2003 |
| WO | WO03094861 A2 | 11/2003 |
| WO | WO03106430 A1 | 12/2003 |
| WO | WO2004054515 A2 | 7/2004 |
| WO | WO2004065370 A1 | 8/2004 |
| WO | WO2004096793 A1 | 11/2004 |
| WO | WO2004098494 A2 | 11/2004 |
| WO | WO2007093402 A1 | 8/2007 |

OTHER PUBLICATIONS

Alexy, et al., "Inhibition of ADP-Evoked Platelet Aggregation by Selected Poly(ADP-Ribose) Polymerase Inhibitors," J Cardiovasc Pharmacol, 2004, 43, pp. 423-431.
Amundson et al., "An Informatics Approach Identifying Markers of Chemosensitivity in Human Cancer Cell Lines," Cancer Research, 2000, 60, pp. 6101-6110.
Ansel Howard C., et al., "Ansel's Pharmaceutical Dosage Forms and Drug Delivery Systems, Table of Contents," 2005, Eigth Edition, Lippincott willams & willkins.
Burkart, et al., "Mice lacking the poly (ADP-ribose) polymerase gene are resistant to pancreatic beta-cell destruction and diabetes development induced by streptozocin," Nature Medicine, 1999, 5 (3), 314-319.
Chen G., et al., "Potentiation of the antitumor activity of cisplatin in mice by 3-am inobenzamide and nicotinamide", Cancer Chemotherapy and Pharmacology, 1988, vol. 22 (4), pp. 303-307.
Cross L.C., et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Cuzzocrea, S., et al., "Protective effects of 3-aminobenzamide, an inhibitor of poly (ADP-ribose) synthase in a carrageenan-induced model of local inflammation," European Journal of Pharmacology, 1998, 342, pp. 67-76.
Ehrlich, W., et al., "Inhibition of the induction of collagenase by interleukin-1β in cultured rabbit synovial fibroblasts after treatment with the poly(ADP-ribose)-polymerase inhibitor 3-aminobenzamide," Rheumatol Int, 1995, 15, pp. 171-172.
Gilchrist et al., "Cyclisation of Ortho-Substituted N-Arylbenzimidoyl Nitrenes. Part 2.1 Preferential Cyclizations at an Ortho-Position Bearing a Methoxycarbonyl Group",, J of the Chem Soci Perkin , 1979, pp. 2303-2307. Griffin, et al., "Novel Benzimidazole and Quinazolinone Inhibitors of the DNA Repair Enzyme Poly(ADP-ribosc)polymcrasc," Pharmaceutical Sciences, 1996, 2 Issue 1 , pp. 43-47.
Holzelova et al., "Autoimmune Lymphoproliferative Syndrome with Somatic Fas Mutations," New England Journal of Medicine, 2004, 351, pp. 1409-1418.
Hoover J.E, Remington's Pharmaceutical Sciences, Tbl of Cont, 1975.
Kroger, H., et al., "Synergistic effects of thalidomide and poly(ADP-rose) polymerase inhibition on type li collagen-induced arthristis in mice ," Inflammation, 1996, 20—Issue 2, pp. 203-215.

(Continued)

Primary Examiner — Kamal Saeed
Assistant Examiner — Nyeemah A Grazier
(74) Attorney, Agent, or Firm — Susan L. Steele

(57) ABSTRACT

Inhibitors of poly(ADP-ribose)polymerase having a structure of Formula (I), ways to make them and methods of treating patients using them are disclosed.

11 Claims, No Drawings

OTHER PUBLICATIONS

Ohkura, et al., "Mechanism of the Color Reaction between m-Dinitrobenzene and Alkali Cyanide. II. Color Reaction Products of 2,4-Dinitroaniline with Postassium Cyanide (Organic Analysis. LXX III )," Chem Pharm Bull, 1970, 18—Issue 11, pp. 2164-2168.

PCT International Search Report for application No. PCT/US2010/020878, Mailed on Dec. 4, 2010, 2 pages.

Poste et al., "Lipid Vesicles as Carriers for Introducing Biologically Active Materials into Cells," Methods in Cell Biology, 1976, 4 (14), Academic Press, 33-71.

Puck, et al., "Immune Disorders Caused by Defects in the Caspase Cascade," Current Allergy and Asthma Reports, 2003, 3, pp. 378-384.

Rengan. et al., "Actin cytoskeletal function is spared, but apoptosis is increased, in WAS patient hematopoietic cells," Blood, 2000, 95 - Issue 4, pp. 1283-1292.

Shimazaki et al., "Evaluation of apoptosis as a prognostic factor in myelodysplastic syndromes", British J Haematology, 2000, 110 Issue 3, pp. 584-590.

Szabo, C., et al., "Protection against peroxynitrite-induced fibroblast injury and arthritis development by inhibition of poly(ADP-ribose) synthase," Proc Natl Acad Sci USA, 1998, 95, pp. 3867-3872.

Thiemermann, C., et al., "Inhibition of the activity of poly (ADP ribose) synthhetase reduces ischemia-reperfusion injury in the heart and skeletal muscle," Proc. Natal. Acad. Sci. USA, 1997, 94, pp. 679-683.

Weltin, et al., "Immunosuppressive Activities of 6(5H)-Phenanthridinone, A New Polu(ADP-Ribose)Polumerase Inhibitor," Int J Immunopharmac., 1995, 17—Issue4, pp. 265-271.

White A.W. et al., "Potentiation of cytotoxic drug activity in human cell lines, by amine substituted 2-arylbenzimidazole-4-carboxamide PARP-1 inhibitors.," Bioorganic and Medicinal Chemistry Letters, 2004, 14 (10), pp. 2433-2437.

BENZTHIAZOLE INHIBITORS OF POLY(ADP-RIBOSE)POLYMERASE

CROSS-REFERENCE TO RELATED APPLICATIONS

This application claims priority to U.S. provisional application Ser. No. 61/145,640, filed Jan. 19, 2009.

FIELD OF THE INVENTION

This invention relates to inhibitors of poly(ADP-ribose) polymerase, ways to make them and methods of treating patients using them.

BACKGROUND OF THE INVENTION

Poly(ADP-ribose)polymerase (PARP) is essential for facilitating DNA repair, controlling RNA transcription, mediating cell death and regulating immune response. This activity makes PARP inhibitors targets for a number of disorders. PARP inhibitors have shown utility for treating diseases such as ischemia reperfusion injury, inflammatory disease, retroviral infections, ischemia reperfusion injury, myocardial infarction, stroke and other neural trauma, organ transplantation, reperfusion of the eye, kidney, gut and skeletal muscle, arthritis, gout, inflammatory bowel disease, CNS inflammation such as MS and allergic encephalitis, sepsis, septic shock, hemmorhagic shock, pulmonary fibrosis, and uveitis, diabetes and Parkinsons disease, liver toxicity following acetominophen overdose, cardiac and kidney toxicities from doxorubicin and platinum-based antineoplastic agents and skin damage secondary to sulfur mustards. PARP inhibitors have also been shown to potentiate radiation and chemotherapy by increasing cell death of cancer cells, limiting tumor growth, decreasing metastasis, and prolonging the survival of tumor-bearing animals. WO 2002/051821 describes compounds having the general structure:

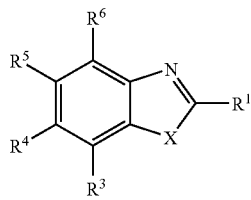

as ER-β-selective ligands. WO 2003/050095 describes compounds having the general structure:

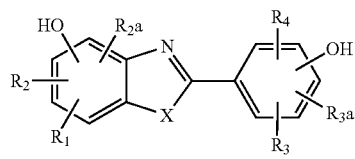

as estrogen receptor modulators.

There is therefore a need in the therapeutic arts for PARP inhibitors. Such compounds can be used to treat subjects suffering from cancer, and can further expand the range of treatment options available for such subjects.

SUMMARY OF THE INVENTION

The present invention has numerous embodiments. One embodiment of this invention, therefore, pertains to compounds that inhibit the activity of poly(ADP-ribose) polymerase and have Formula I

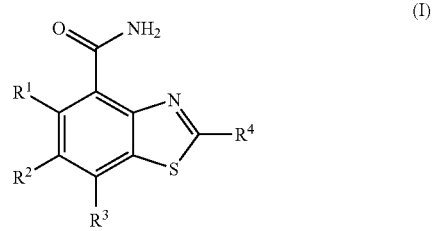

wherein $R^1$, $R^2$, $R^3$ and $R^4$ are as described herein, and therapeutically acceptable salts thereof.

Another embodiment pertains to a compound selected from the group consisting of and therapeutically acceptable salts thereof.

Another embodiment pertains to a pharmaceutical composition comprising a compound having the structure of Formula I. This invention also is directed to a use of one or more compounds and/or salts of the invention to prepare a medicament.

Another embodiment pertains to methods of treating a condition in a subject by administering a therapeutically effective amount of a compound having the structure of Formula I to the subject.

Another embodiment comprises pharmaceutical compositions comprising a compound having Formula I and an excipient.

Still another embodiment comprises methods of inhibiting PARP in a mammal comprising administering thereto a therapeutically acceptable amount of a compound having formula I.

Still another embodiment comprises methods of treating cancer in a mammal comprising administering thereto a therapeutically acceptable amount of a compound having formula I.

Still another embodiment comprises methods for decreasing tumor volume in a mammal comprising administering thereto a therapeutically acceptable amount of a compound having formula I Still another embodiment comprises the use of a compound of Formula I for the preparation of a medicament for the treatment of cancer.

Still another embodiment comprises a method of treating leukemia, colon cancer, glioblastomas, lymphomas, melanomas, carcinomas of the breast, carcinomas of the prostate or cervical carcinomas in a mammal comprising administering thereto a therapeutically acceptable amount of a compound having formula I.

Still another embodiment comprises the use of a compound of Formula I for the preparation of a medicament for the treatment of leukemia, colon cancer, glioblastomas, lymphomas, melanomas, carcinomas of the breast, carcinomas of the prostate or cervical carcinomas.

Still another embodiment comprises methods for potentiation of cytotoxic cancer therapy in a mammal comprising administering thereto a therapeutically acceptable amount of a compound having formula I.

Still another embodiment comprises methods for potentiation of radiation therapy in a mammal comprising administering thereto a therapeutically acceptable amount of a compound having formula I.

Still another embodiment comprises methods of treating ischemia reperfusion injury associated with myocardial infarction, stroke, neural trauma or organ transplantation in a mammal comprising administering thereto a therapeutically acceptable amount of a compound having formula I.

Still another embodiment comprises methods of treating reperfusion of the eye, kidney, gut or skeletal muscle in a mammal comprising administering thereto a therapeutically acceptable amount of a compound having formula I.

Still another embodiment comprises methods of treating arthritis, gout, inflammatory bowel disease, CNS inflammation, multiple sclerosis, allergic encephalitis, sepsis, septic shock, hemmorhagic shock, pulmonary fibrosis or uveitis in a mammal comprising administering thereto a therapeutically acceptable amount of a compound having formula I.

Still another embodiment comprises a method of treating rheumatoid arthritis or septic shock in a mammal comprising administering thereto a therapeutically acceptable amount of a compound having formula I.

Still another embodiment comprises methods of treating diabetes or Parkinsons disease in a mammal comprising administering thereto a therapeutically acceptable amount of a compound having formula I.

Still another embodiment comprises methods of treating hypoglycemia in a mammal comprising administering thereto a therapeutically acceptable amount of a compound having formula I.

Still another embodiment comprises methods of treating retroviral infection in a mammal comprising administering thereto a therapeutically acceptable amount of a compound having formula I.

Still another embodiment comprises methods of treating liver toxicity following acetominophen overdose in a mammal comprising administering thereto a therapeutically acceptable amount of a compound having formula I.

Still another embodiment comprises a method of treating cardiac or kidney toxicities from doxorubicin or platinum based antineoplastic agents in a mammal comprising administering thereto a therapeutically acceptable amount of a compound having formula I.

Still another embodiment comprises methods of treating skin damage secondary to sulfur mustards in a mammal comprising administering thereto a therapeutically acceptable amount of a compound having formula I.

Still another embodiment comprises the compounds
4-[4-(aminocarbonyl)-1,3-benzothiazol-2-yl]phenyl trifluoromethanesulfonate;
2-(1,1'-biphenyl-4-yl)-1,3-benzothiazole-4-carboxamide;
2-(4-pyridin-3-ylphenyl)-1,3-benzothiazole-4-carboxamide;
2-(4-pyridin-4-ylphenyl)-1,3-benzothiazole-4-carboxamide; and
2-[(2S)-2-methylpyrrolidin-2-yl]-1,3-benzothiazole-4-carboxamide.

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

A. Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight- or branched-chain saturated hydrocarbyl substituent typically containing from 1 to about 20 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 20 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 20 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 7 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl (tetralinyl), indenyl, indanyl (dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 7 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —NH$_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

A substituent is "substitutable" if it comprises at least one carbon or nitrogen atom that is bonded to one or more hydrogen atoms. Thus, for example, hydrogen, halogen, and cyano do not fall within this definition. In addition, a sulfur atom in a heterocyclyl containing such atom is substitutable with one or two oxo substituents.

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated). If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxy" (alone or in combination with another term(s)) means an ether substituent, and may be depicted as —O—.

The term "alkyloxy" (alone or in combination with another term(s)) means an alkylether substituent, i.e., —O-alkyl.

Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl-NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4-b]-N-pyridinyl, pyrido[3,2-b]-N-pyridinyl, or pyrido[4,3-b]-N-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$— prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

B. Compounds

Embodiments of Formula I

In one embodiment, the present invention is directed, in part, to a class of compounds having a structure of Formula I

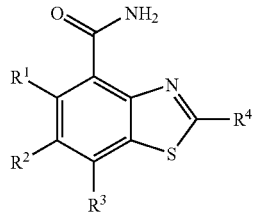

Formula (I)

wherein $R^1$, $R^2$, and $R^3$ are independently selected from the group consisting of hydrogen, halogen, cyano, nitro, alkyl, alkenyl, alkynyl, alkoxy, haloalkyl, haloalkoxy, hydroxyalkyl, $R^7(O)CO(O)R^8$, $NR^7R^8$, and —$C(O)NR^7R^8$; wherein $R^7$ and $R^8$ are selected from the group consisting of hydrogen and alkyl;

$R^4$ is selected from the group consisting of alkyl, alkenyl, alkynyl, cycloalkyl, cycloalkenyl, heterocyclyl and aryl wherein (a) the $R^4$ alkyl, alkenyl, alkynyl substituents are optionally substituted with one or more substituents selected from the group consisting of $R^6$, halogen, cyano, oxo, —$OR^{10}$, —$C(O)R^{10}$, —$C(O)OR^{10}$, —$OC(O)R^{10}$, —$NR^{11}R^{12}$, —$NR^{11}C(O)R^{12}$, —$NHC(O)NHR^{11}$, —$C(O)NR^{11}R^{12}$, —$SR^{10}$, —$S(O)R^{10}$, —$SO_2R^{10}$, —$OC(O)OR^{10}$, —$SR_2NR^{11}R^{12}$, —$N_3$, —$NO_2$, —$CF_3$, —$CF_2CF_3$, —$OCF_3$, and —$OCF_2CF_3$; (b) wherein the $R^4$ cycloalkyl, cycloalkenyl, aryl, and heterocyclyl substituents are optionally substituted with one or more $R^5$;

$R^5$ is selected from the group consisting of $R^6$, alkyl, alkenyl, alkynyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{14}$, —$C(O)NR^{14}R^{15}$, —$SR^{13}$, —$S(O)R^{13}$, —$OS(O)_2CF_3$, —$SO_2R^{13}$, —$OC(O)OR^{13}$, —$SO_2NR^{14}R^{15}$, —$N_3$, —$NO_2$, —$CF_3$, —$CF_2CF_3$, —$OCF_3$, and —$OCF_2CF_3$ wherein the $R^5$ alkyl, alkenyl, and alkynyl substituents are optionally substituted with one or more substituents selected from the group consisting of aryl, heterocyclyl, cycloalkyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{13}$ and —$C(O)NR^{14}R^{15}$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —$OR^{16}$, —$C(O)R^{16}$, —$C(O)OR^{16}$, —$OC(O)R^{16}$, —$NR^{17}R^{18}$, —$NR^{17}C(O)R^{18}$, —$NHC(O)NHR^{17}$, —$C(O)NR^{17}R^{18}$, $SR^{16}$, $S(O)R^{16}$, $SO_2R^{16}$, $OC(O)OR^{16}$, $SO_2NR^{17}R^{18}$, —$N_3$, —$NO_2$, —$CF_3$, —$CF_2CF_3$, —$OCF_3$, and —$OCF_2CF_3$;

$R^{10}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{11}$ and $R^{12}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

Embodiments of $R^1$, $R^2$ and $R^3$ in Formula I

In one embodiment of Formula I, $R^1$, $R^2$ and $R^3$ are selected from the group consisting of hydrogen, halogen and $C_1$ to $C_3$ alkyl. In another embodiment of Formula I, $R^1$, $R^2$ and $R^3$ are selected from the group consisting of hydrogen, fluoro, chloro and methyl. In another embodiment of Formula I, at least 1 of $R^1$, $R^2$ and $R^3$ are hydrogen. In another embodiment of Formula I, at least 2 of $R^1$, $R^2$ and $R^3$ are hydrogen. In another embodiment, each of $R^1$, $R^2$ and $R^3$ are hydrogen, as described in Formula II:

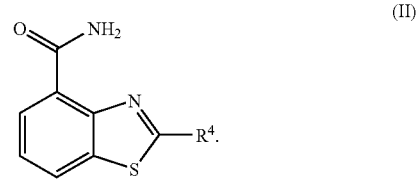

(II)

Embodiments of Formula II

In one embodiment, the present invention is directed, in part, to a class of compounds having a structure of Formula II,

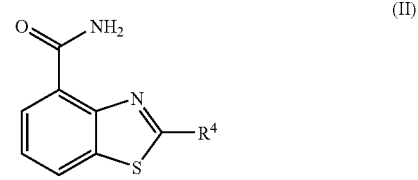

(II)

wherein $R^4$ is selected from the group consisting of alkyl, alkenyl, alkynyl, cycloalkyl, cycloalkenyl, heterocyclyl and aryl wherein (a) the $R^4$ alkyl, alkenyl, and alkynyl substituents are optionally substituted with $R^6$ and further unsubstituted or substituted with one or more substituents selected from the group consisting of alkyl, alkenyl, alkynyl, halogen, cyano, oxo, $-OR^{10}$, $-C(O)R^{10}$, $-C(O)OR^{10}$, $-OC(O)R^{10}$, $-NR^{11}R^{12}$, $-NR^{11}C(O)R^{12}$, $-NHC(O)NHR^{11}$, $-C(O)NR^{11}R^{12}$, $-S(O)R^{10}$, $-SO_2R^{10}$, $-OC(O)OR^{10}$, $-SO_2NR^{11}R^{12}$, $-N_3$, $-NO_2$, $-CF_3$, $-CF_2CF_3$, $-OCF_3$, and $-OCF_2CF_3$ (b) wherein the $R^4$ cycloalkyl, cycloalkenyl, aryl, and heterocyclyl substituents are optionally substituted with one or more $R^5$;

$R^5$ is selected from the group consisting of $R^6$, alkyl, alkenyl, alkynyl, halogen, cyano, oxo, $-OR^{13}$, $-C(O)R^{13}$, $-C(O)OR^{13}$, $-OC(O)R^{13}$, $-NR^{14}R^{15}$, $-NR^{14}C(O)R^{15}$, $-NHC(O)NHR^{14}$, $-C(O)NR^{14}R^{15}$, $-SR^{13}$, $-S(O)R^{13}$, $-OS(O)_2CF_3$, $-SO_2R^{13}$, $-OC(O)OR^{13}$, $-SO_2NR^{14}R^{15}$, $-N_3$, $-NO_2$, $-CF_3$, $-CF_2CF_3$, $-OCF_3$, and $-OCF_2CF_3$ wherein the $R^5$ alkyl, alkenyl, and alkynyl substituents are optionally substituted with one or more substituents selected from the group consisting of aryl, heterocyclyl, cycloalkyl, halogen, cyano, oxo, $-OR^{13}$, $-C(O)R^{13}$, $-C(O)OR^{13}$, $-OC(O)R^{13}$, $-NR^{14}R^{15}$, $-NR^{14}C(O)R^{15}$, $-NHC(O)NHR^{13}$ and $-C(O)NR^{14}R^{15}$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, $-OR^{16}$, $-C(O)R^{16}$, $-C(O)OR^{16}$, $-OC(O)R^{16}$, $-NR^{17}R^{18}$, $-NR^{17}C(O)R^{18}$, $-NHC(O)NHR^{17}$, $-C(O)NR^{17}R^{18}$ is $SR^{16}$, $S(O)R^{16}$, $SO_2R^{16}$, $OC(O)OR^{16}$, $SO_2NR^{17}R^{18}$, $-N_3$, $-NO_2$, $-CF_3$, $-CF_2CF_3$, $-OCF_3$, and $-OCF_2CF_3$;

$R^{10}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{11}$ and $R^{12}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

Embodiments of $R^4$ in Formula II

In one embodiment of Formula II, $R^4$ is selected from the group consisting of alkyl, alkenyl, cycloalkyl, cycloalkenyl, 3, 4, 5, 6, 7, 8, 9 or 10 membered ring heterocyclyl and aryl, optionally substituted as described in Formula II. In another embodiment $R^4$ is selected from the group consisting of alkyl, cycloalkyl, cycloalkenyl, 4, 5, 6, 7, or 8 membered ring heterocyclyl and aryl, optionally substituted as described in Formula II. In another embodiment $R^4$ is selected from the group consisting of alkyl, cycloalkyl, cycloalkenyl, 4, 5, 6, or 7 membered ring heterocyclyl and aryl, optionally substituted as described in Formula II. In another embodiment $R^4$ is selected from the group consisting of alkyl, cycloalkyl, cycloalkenyl, 5 or 6 membered ring heterocyclyl and aryl, optionally substituted as described in Formula II. In another embodiment $R^4$ is selected from the group consisting of 5 to 6 membered ring heterocyclyl and aryl, optionally substituted as described in Formula II. In another embodiment $R^4$ is 5 to 6 membered ring heterocyclyl, optionally substituted as described in Formula II.

In one embodiment of Formula II, $R^4$ is selected from the group consisting of alkyl, heterocyclyl and aryl wherein (a) the $R^4$ alkyl substituent is optionally substituted with $R^6$ and further unsubstituted or substituted with one or more substituents selected from the group consisting of alkyl, alkenyl, alkynyl, halogen, cyano, oxo, $-OR^{10}$, $-C(O)R^{10}$, $-C(O)OR^{10}$, $-OC(O)R^{10}$, $-NR^{11}R^{12}$, $-NR^{11}C(O)R^{12}$, $-NHC(O)NHR^{11}$, $-C(O)NR^{11}R^{12}$, $-SR^{10}$, $-S(O)R^{10}$, $-SO_2R^{10}$, $-OC(O)OR^{10}$, $-SO_2NR^{11}R^{12}$, $-N_3$, $-NO_2$, $-CF_3$, $-CF_2CF_3$, $-OCF_3$, and $-OCF_2CF_3$ (b) wherein the $R^4$ aryl and heterocyclyl substituents are optionally substituted with one or more $R^5$; wherein $R^5$ is as described in Formula II. In one embodiment, of Formula II, $R^4$ is selected from the group consisting of phenyl, azetidinyl, pyrrolidinyl, imidazolidinyl, pyrazolidinyl, piperadinyl, and piperazinyl.

In one embodiment, of Formula II, $R^4$ is selected from the group consisting of

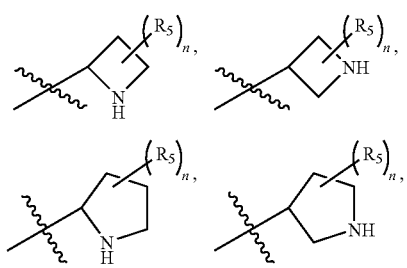

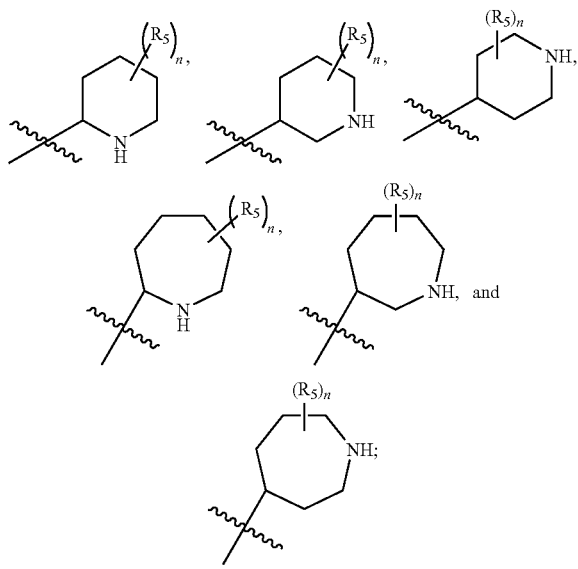

wherein n is 0 to 3, and $R^5$ is as described in Formula II.

In one embodiment, of Formula II, $R^4$ is selected from the group consisting of

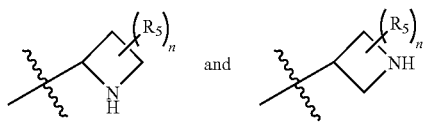

wherein n is 0 to 2, and $R^5$ is as described in Formula II. In another embodiment of Formula II, $R^4$ is selected from the group consisting of

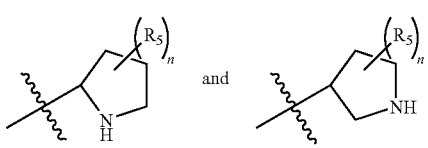

wherein n is 0 to 3, and $R^5$ is as described in Formula II. In another embodiment of Formula II, $R^4$ is

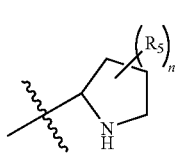

wherein n is 0 to 3, and $R^5$ is as described in Formula II. In another embodiment of Formula II, $R^4$ is

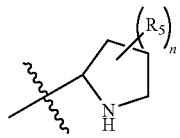

wherein n is 1, and $R^5$ is as described in Formula II. In another embodiment of Formula II, $R^4$ is

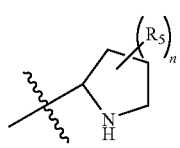

wherein n is 1, and $R^5$ is alkyl. In another embodiment of Formula II, $R^4$ is

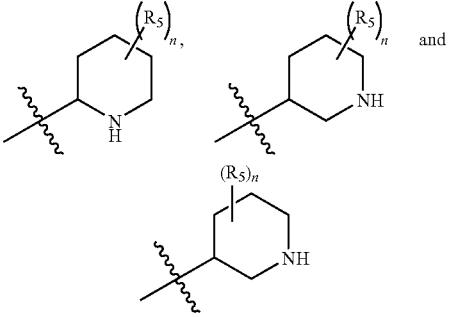

wherein n is 1, and $R^5$ is methyl. In another embodiment of Formula II, $R^4$ is selected from the group consisting of

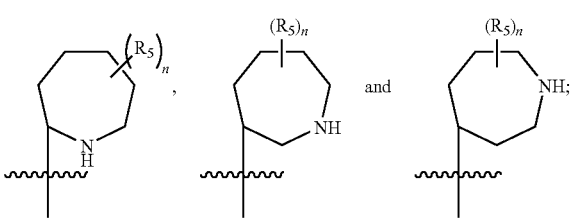

wherein n is 0 to 3, and $R^5$ is as described in Formula II. In another embodiment of Formula II, $R^4$ is selected from the group consisting of wherein n is 0 to 3, and $R^5$ is as described in Formula II. In another embodiment of Formula II, $R^4$ is selected from the group consisting of phenyl and

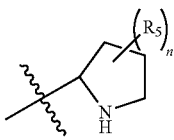

wherein $R^5$ and n are as described in Formula I. In another embodiment of Formula II, $R^4$ is selected from the group consisting of phenyl optionally substituted with one or more $R^5$ and

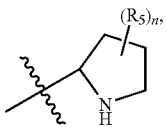

wherein $R^5$ is selected from the group consisting of $R^6$, unsubstituted alkyl, and —OS(O)$_2$CF$_3$, wherein $R^6$ is unsubstituted phenyl or an unsubstituted heterocyclyl selected from the group consisting of

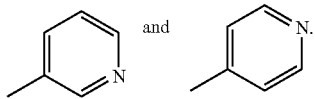

In another embodiment of Formula II, $R^4$ is selected from the group consisting of phenyl and

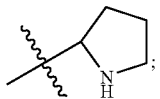

each optionally substituted with one to three $R^5$, wherein $R^5$ is selected from the group consisting of $R^6$, unsubstituted alkyl, and —OS(O)$_2$CF$_3$, wherein $R^6$ is unsubstituted phenyl or an unsubstituted heterocyclyl selected from the group consisting of

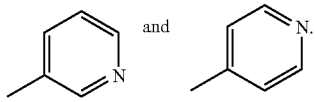

In another embodiment $R^4$ is aryl, optionally substituted as described in Formula II. In another embodiment $R^4$ is selected from the group consisting of phenyl and napthyl, optionally substituted as described in Formula II. In another embodiment, $R^4$ is phenyl, optionally substituted as described in Formula III:

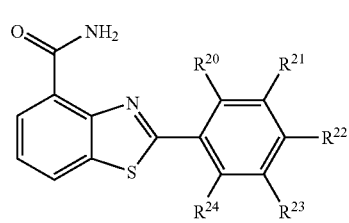

wherein $R^{20}$, $R^{21}$, $R^{22}$, $R^{23}$ and $R^{24}$ are independently selected from the group consisting of hydrogen, $R^6$, alkyl, alkenyl, alkynyl, halogen, cyano, oxo, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{14}$, —C(O)NR$^{14}$R$^{15}$, —SR$^{13}$, —S(O)R$^{13}$, —OS(O)$_2$CF$_3$, —SO$_2$R$^{13}$, —OC(O)OR$^{13}$, —SO$_2$NR$^{14}$R$^{15}$, —N$_3$, —NO$_2$, —CF$_3$, —CF$_2$CF$_3$, —OCF$_3$, and —OCF$_2$CF$_3$ wherein the alkyl, alkenyl, and alkynyl substituents are optionally substituted with one or more substituents selected from the group consisting of aryl, heterocyclyl, cycloalkyl, halogen, cyano, oxo, —OR$^{13}$, —C(O)R$^{13}$, —C(O)OR$^{13}$, —OC(O)R$^{13}$, —NR$^{14}$—NR$^{15}$, —NHC(O)NHR$^{13}$ and —C(O)NR$^{14}$R$^{15}$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —OR$^{16}$, —C(O)R$^{16}$, —C(O)OR$^{16}$, —OC(O)R$^{16}$, —NR$^{17}$R$^{18}$, —NR$^{17}$C(O)R$^{18}$, —NHC(O)NHR$^{17}$, —C(O)NR$^{17}$R$^{18}$, SR$^{16}$, S(O)R$^{16}$, SO$_2$R$^{16}$, OC(O)OR$^{16}$, SO$_2$NR$^{17}$R$^{18}$, —N$_3$, —NO$_2$, —CF$_3$, —CF$_2$CF$_3$, —OCF$_3$, and —OCF$_2$CF$_3$;

$R^{10}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{11}$ and $R^{12}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

Embodiments of Formula III

In one embodiment, the present invention is directed, in part, to a class of compounds having a structure of Formula III

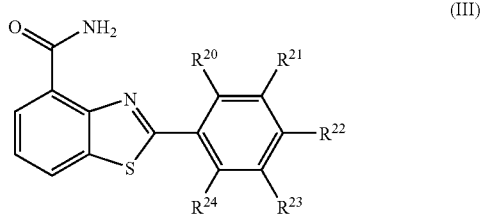

(III)

wherein $R^{20}$, $R^{21}$, $R^{22}$, $R^{23}$ and $R^{24}$ are independently selected from the group consisting of hydrogen, $R^6$, alkyl, alkenyl, alkynyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{14}$, —$C(O)NR^{14}R^{15}$, —$SR^{13}$, —$S(O)R^{13}$, —$OS(O)_2CF_3$, —$SO_2R^{13}$, —$OC(O)OR^{13}$, —$SO_2NR^{14}R^{15}$, —$N_3$, —$NO_2$, —$CF_3$, —$CF_2CF_3$, —$OCF_3$, and —$OCF_2CF_3$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —$OR^{16}$, —$C(O)R^{16}$, —$C(O)OR^{16}$, —$OC(O)R^{16}$, —$NR^{17}R^{18}$, —$NHC(O)NHR^{17}$, —$C(O)NR^{17}R^{18}$, $SR^{16}$, $S(O)R^{16}$, $SO_2R^{16}$, $OC(O)OR^{16}$, $SO_2NR^{17}R^{18}$, —$N_3$, —$NO_2$, —$CF_3$, —$CF_2CF_3$, —$OCF_3$, and —$OCF_2CF_3$;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

In one embodiment of Formula III, at least 1 of $R^{20}$, $R^{21}$, $R^{22}$, $R^{23}$ and $R^{24}$ are hydrogen. In another embodiment of Formula III, at least 2 of $R^{20}$, $R^{21}$, $R^{23}$ and $R^{24}$ are hydrogen. In another embodiment of Formula III, at least 3 of $R^{20}$, $R^{21}$, $R^{23}$ and $R^{24}$ are hydrogen. In another embodiment of Formula III, $R^{20}$, $R^{21}$, $R^{23}$ and $R^{24}$ are each hydrogen. In another embodiment of Formula III, at least 2 of $R^{20}$, $R^{21}$, $R^{23}$ and $R^{24}$ are hydrogen, and $R^{22}$ is selected from the group consisting of $R^6$, alkyl, alkenyl, alkynyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{14}$, —$C(O)NR^{14}R^{15}$, —$SR^{13}$, —$S(O)R^{13}$, —$OS(O)_2CF_3$, —$SO_2R^{13}$, —$OC(O)OR^{13}$, —$SO_2NR^{14}R^{15}$, —$N_3$, —$NO_2$, —$CF_3$, —$CF_2CF_3$, —$OCF_3$, and —$OCF_2CF_3$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —$OR^{16}$, —$C(O)R^{16}$, —$C(O)OR^{16}$, —$OC(O)R^{16}$, —$NR^{17}R^{18}$, —$NR^{17}C(O)R^{18}$, —$NHC(O)NHR^{17}$, —$C(O)NR^{17}R^{18}$, $SR^{16}$, $S(O)R^{16}$, $SO_2R^{16}$, $OC(O)OR^{16}$, $SO_2NR^{17}R^{18}$, —$N_3$, —$NO_2$, —$CF_3$, —$CF_2CF_3$, —$OCF_3$, and —$OCF_2CF_3$;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

In another embodiment of Formula III, at least 2 of $R^{20}$, $R^{21}$, $R^{23}$ and $R^{24}$ are hydrogen, and $R^{22}$ is selected from the group consisting of $R^6$, alkyl, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{14}$, —$C(O)NR^{14}R^{15}$, —$SR^{13}$, —$S(O)R^{13}$, —$OS(O)_2CF_3$, —$SO_2R^{13}$, —$OC(O)OR^{13}$, —$SO_2NR^{14}R^{15}$, —$NO_2$, —$CF_3$, —$CF_2CF_3$, —$OCF_3$, and —$OCF_2CF_3$;

$R^6$ is aryl or heterocyclyl wherein the $R^6$ aryl and heterocyclyl substituents are optionally substituted from the group consisting of alkyl, alkenyl, alkynyl, aminoalkyl, halogen, cyano, oxo, —OR$^{16}$, —C(O)R$^{16}$, —C(O)OR$^{16}$, —OC(O)R$^{16}$, —NR$^{17}$R$^{18}$, —NR$^{17}$C(O)R$^{18}$, —NHC(O)NHR$^{17}$, —C(O)NR$^{17}$R$^{18}$, SR$^{16}$, S(O)R$^{16}$, SO$_2$R$^{16}$, OC(O)OR$^{16}$, SO$_2$NR$^{17}$R$^{18}$, —N$_3$, —NO$_2$, —CF$_3$, —CF$_2$CF$_3$, —OCF$_3$, and —OCF$_2$CF$_3$;

R$^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

R$^{14}$ and R$^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

R$^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and R$^{17}$ and R$^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

In another embodiment of Formula III, at least 2 of R$^{20}$, R$^{21}$, R$^{23}$ and R$^{24}$ are hydrogen, and R$^{22}$ is selected from the group consisting of R$^6$, alkyl, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{14}$, —C(O)NR$^{14}$R$^{15}$, —SR$^{13}$, —S(O)R$^{13}$, —OS(O)$_2$CF$_3$, —SO$_2$R$^{13}$, —OC(O)OR$^{13}$, —SO$_2$NR$^{14}$R$^{15}$, —N$_3$, —NO$_2$, —CF$_3$, —CF$_2$CF$_3$, —OCF$_3$, and —OCF$_2$CF$_3$ R$^6$ is phenyl or 5, 6 or 7-membered heterocyclyl, wherein the R$^6$ phenyl and heterocyclyl substituents are optionally substituted with one or more substituents independently selected from the group consisting of alkyl, alkenyl, aminoalkyl, halogen, oxo, —OR$^{16}$, —C(O)R$^{16}$, —C(O)OR$^{16}$, —NR$^{17}$R$^{18}$, —NR$^{17}$C(O)R$^{18}$, —C(O)NR$^{17}$R$^{18}$, SR$^{16}$, S(O)R$^{16}$, SO$_2$R$^{16}$, SO$_2$NR$^{17}$R$^{18}$, —CF$_3$, and OCF$_3$;

R$^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

R$^{14}$ and R$^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

R$^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and R$^{17}$ and R$^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

In another embodiment of Formula III, R$^{20}$, R$^{21}$, R$^{23}$ and R$^{24}$ are each hydrogen, as described in Formula IV:

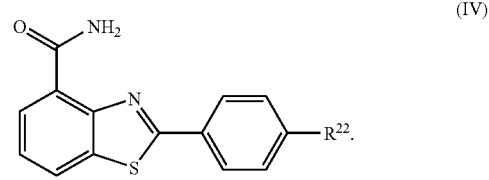

(IV)

Embodiments of Formula IV

In one embodiment, the present invention is directed, in part, to a class of compounds having a structure of Formula IV:

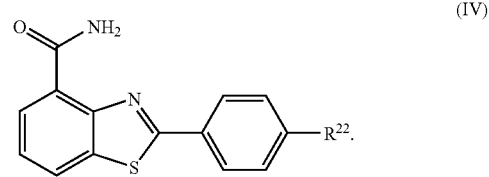

(IV)

wherein R$^{22}$ is selected from the group consisting of R$^6$, alkyl, alkenyl, alkynyl, halogen, cyano, oxo, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{14}$, —C(O)NR$^{14}$R$^{15}$, —SR$^{13}$, —S(O)R$^{13}$, —OS(O)$_2$CF$_3$, —SO$_2$R$^{13}$, —OC(O)OR$^{13}$, —SO$_2$NR$^{14}$R$^{15}$, —N$_3$, —NO$_2$, —CF$_3$, —CF$_2$CF$_3$, —OCF$_3$, and —OCF$_2$CF$_3$ wherein the R$^{22}$ alkyl, alkenyl, and alkynyl substituents are optionally substituted with one or more substituents selected from the group consisting of aryl, heterocyclyl, cycloalkyl, halogen, cyano, oxo, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{13}$ and —C(O)NR$^{14}$R$^{15}$;

R$^6$ is aryl or heterocyclyl wherein the R$^6$ aryl and heterocyclyl substituents are optionally substituted with one or more substituents independently selected from the group consisting of alkyl, alkenyl, alkynyl, aminoalkyl, halogen, cyano, oxo, —OR$^{16}$, —C(O)R$^{16}$, —C(O)OR$^{16}$, —OC(O)R$^{16}$, —NR$^{17}$R$^{18}$, —NR$^{17}$C(O)R$^{18}$, —NHC(O)NHR$^{17}$, —C(O)NR$^{17}$R$^{18}$, SR$^{16}$, S(O)R$^{16}$, SO$_2$R$^{16}$, OC(O)OR$^{16}$, SO$_2$NR$^{17}$R$^{18}$, —N$_3$, —NO$_2$, —CF$_3$, —CF$_2$CF$_3$, —OCF$_3$, and —OCF$_2$CF$_3$;

R$^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

In another embodiment of Formula IV, $R^{22}$ is selected from the group consisting of $R^6$, alkyl, alkenyl, halogen, cyano, oxo, $-OR^{13}$, $-C(O)R^{13}$, $-C(O)OR^{13}$, $-OC(O)R^{13}$, $-NR^{14}R^{15}$, $-NR^{14}C(O)R^{15}$, $-C(O)NR^{14}R^{15}$, $-SR^{13}$, $-S(O)R^{13}$, $-OS(O)_2CF_3$, $-SO_2R^{13}$ and $-OCF_3$, wherein the $R^{22}$ alkyl and alkenyl substituents are optionally substituted with one or more substituents selected from the group consisting of aryl, heterocyclyl, cycloalkyl, oxo, $-OR^{13}$, $-C(O)R^{13}$, $-C(O)OR^{13}$ and $-NR^{14}R^{15}$;

$R^6$ is aryl or 3, 4, 5, 6, 7 or 8-membered ring heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, $-OR^{16}$, $-C(O)R^{16}$, $-C(O)OR^{16}$, $-OC(O)R^{16}$, $-NR^{17}R^{18}$, $-NR^{17}C(O)R^{18}$, $-NHC(O)NHR^{17}$, $-C(O)NR^{17}R^{18}$, $SR^{16}$, $S(O)R^{16}$, $SO_2R^{16}$, $OC(O)OR^{16}$, $SO_2NR^{17}R^{18}$, $-N_3$, $-NO_2$, $-CF_3$, $-CF_2CF_3$, $-OCF_3$, and $-OCF_2CF_3$;

$R^{10}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{11}$ and $R^{12}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo.

In another embodiment of Formula IV, $R^{22}$ is selected from the group consisting of $R^6$, alkyl, alkenyl, halogen, cyano, oxo, $-OR^{13}$, $-C(O)R^{13}$, $-C(O)OR^{13}$, $-OC(O)R^{13}$, $-NR^{14}R^{15}$, $-NR^{14}C(O)R^{15}$, $-NHC(O)NHR^{14}$, $-C(O)NR^{14}R^{15}$, $-SR^{13}$, $-S(O)R^{13}$, $-OS(O)_2CF_3$, $-SO_2R^{13}$, $-OC(O)OR^{13}$, $-SO_2NR^{14}R^{15}$, $-N_3$, $-NO_2$, $-CF_3$, $-CF_2CF_3$, $-OCF_3$, and $-OCF_2CF_3$ wherein the $R^{22}$ alkyl, alkenyl, and alkynyl substituents are optionally substituted with one or more substituents selected from the group consisting of aryl, heterocyclyl, cycloalkyl, halogen, cyano, oxo, $-OR^{13}$, $-C(O)R^{13}$, $-C(O)OR^{13}$, $-OC(O)R^{13}$, $-NR^{14}R^{15}$, $-NR^{14}C(O)R^{15}$, $-NHC(O)NHR^{13}$ and $-C(O)NR^{14}R^{15}$;

$R^6$ is aryl or 3, 4, 5, 6, 7 or 8 membered ring heterocyclyl wherein the $R^6$ aryl and heterocyclyl substituents are optionally substituted with one or more substituents independently selected from the group consisting of alkyl, alkenyl, halogen, cyano, oxo, $-OR^{16}$, $-C(O)R^{16}$, $-C(O)OR^{16}$, $-OC(O)R^{16}$, $-NR^{17}R^{18}$, $-NR^{17}R^{18}$, $-NR^{17}C(O)R^{18}$, $-C(O)NR^{17}R^{18}$, $SR^{16}$, $S(O)R^{16}$, $SO_2R^{16}$, $SO_2NR^{17}R^{18}$, $-CF_3$, $-CF_2CF_3$, and $-OCF_3$;

$R^{10}$, at each occurrence, is independently selected from the group consisting of hydrogen and alkyl;

$R^{11}$ and $R^{12}$, at each occurrence, are independently selected from the group consisting of hydrogen and alkyl;

$R^{13}$, at each occurrence, is independently selected from the group consisting of hydrogen and alkyl;

$R^{14}$ and $R^{15}$, at each occurrence, are independently selected from the group consisting of hydrogen and alkyl;

$R^{16}$, at each occurrence, is independently selected from the group consisting of hydrogen and alkyl; and $R^{17}$ and $R^{18}$, at each occurrence, are independently selected from the group consisting of hydrogen and alkyl.

In another embodiment of Formula IV, $R^{22}$ is selected from the group consisting of $R^6$, alkyl, $-OR^{13}$, and $-OS(O)_2CF_3$;

$R^6$ is unsubstituted aryl or unsubstituted 5 or 6 membered ring heterocyclyl;

$R^{13}$ is selected from the group consisting of hydrogen and alkyl.

In another embodiment of Formula IV, $R^{22}$ is selected from the group consisting of $R^6$, alkyl, $-OR^{13}$, and $-OS(O)_2CF_3$;

$R^6$ is selected from the group consisting of unsubstituted aryl and unsubstituted 6 membered ring heterocyclyl;

$R^{13}$ is selected from the group consisting of hydrogen and alkyl.

In another embodiment of Formula IV, $R^{22}$ is selected from the group consisting of $R^6$, alkyl, —$OR^{13}$, and —$OS(O)_2CF_3$;

$R^6$ is unsubstituted phenyl or an unsubstituted heterocyclyl selected from the group consisting of

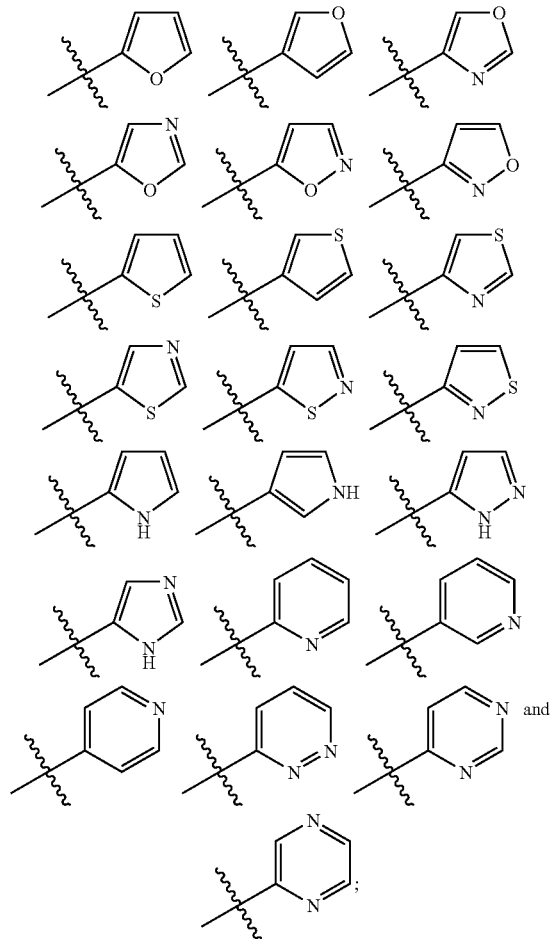

and wherein $R^{13}$ is selected from the group consisting of hydrogen and alkyl.

In another embodiment of Formula IV, $R^{22}$ is selected from the group consisting of $R^6$, alkyl, —$OR^{13}$, and —$OS(O)_2CF_3$;

$R^6$ is unsubstituted phenyl or an unsubstituted heterocyclyl selected from the group consisting of

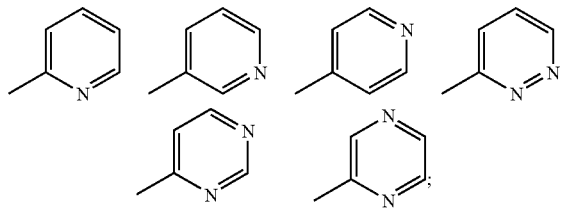

$R^{13}$ is selected from the group consisting of hydrogen and alkyl.

In another embodiment of Formula IV, $R^{22}$ is selected from the group consisting of $R^6$, alkyl, —$OR^{13}$, and —$OS(O)_2CF_3$;

$R^6$ is unsubstituted phenyl or an unsubstituted heterocyclyl selected from the group consisting of

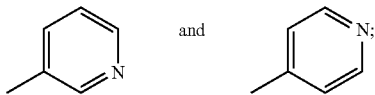

$R^{13}$ is selected from the group consisting of hydrogen and alkyl.

C. Isomers

This invention also is directed, in part, to all isomers of the compounds of formula I (and their salts) (i.e., structural and stereoisomers). Structural isomers include chain and position isomers. Stereoisomers include E/Z isomers (i.e., isomers with regard to one or more double bonds), enantiomers (i.e., stereo-isomers that have opposite configurations at all stereogenic centers), and diastereoisomers (i.e., stereo-isomers that have the same configuration at one or more stereogenic centers, but differ at other stereogenic centers).

D. Salts

This invention also is directed, in part, to all salts of the compounds of formula I. A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula I can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula I include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

E. Purity

Compounds of formula I (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

F. Methods for Preparation of the Compounds and Salts

The starting materials used herein are commercially available or may be prepared by routine methods well known to those of ordinary skill in the art. The exemplified compounds were named using ACD/ChemSketch Version 5.06 (5 Jun. 2001, Advanced Chemistry Development Inc., Toronto, Ontario).

Example 1

4-[4-(aminocarbonyl)-1,3-benzothiazol-2-yl]phenyl trifluoromethanesulfonate

Example 1A

N-(2-bromophenyl)-4-methoxybenzamide

To a suspension of 2-bromoaniline (7.3 mL) and pyridine (13.5 mL) in toluene (110 mL) was added 4-methoxybenzoyl chloride (11 mL) and the mixture was heated at 40° C. for 2.5 hours. The solid was filtered, washed with diethyl ether and water and dried to afford the title compound.

Example 1B

N-(2-bromophenyl)-4-methoxybenzothioamide

To a solution of EXAMPLE 1A (15 g) in toluene (55 mL) was added Lawesson's reagent (11.49 g) and the mixture heated at reflux for 4 hours. The mixture was cooled and concentrated and the residue was dissolved in ethyl acetate and washed with 1N hydrochloric acid and brine. The organic layers were concentrated and the crude material was triturated with ethyl acetate and filtered to afford title compound.

Example 1C 4-bromo-2-(4-methoxyphenyl)benzo[d]thiazole

To a solution of EXAMPLE 1B (7.1 g) in ethanol (26 mL) was added 30% sodium hydroxide (17.63 mL) and the mixture was stirred for 5 minutes. Water (35 mL) was added and 4 mL aliquots of the mixture were added at 1-minute intervals to a heated (85° C.) solution of potassium ferricyanide(III) (29 g) in water (260 mL). The mixture was maintained at 85° C. for 30 minutes and cooled. The precipitate was collected, washed with water and dried to afford the title compound.

Example 1D 2-(4-methoxyphenyl)benzo[d]thiazole-4-carbonitrile

To a solution of EXAMPLE 1C (5 g) in N,N-dimethylformamide (1.6 mL) was added copper(I) cyanide (2.1 g) and the mixture heated at reflux for 6 hours. The mixture was cooled, poured into 1N hydrochloric acid and extracted with ethyl acetate. The solid that precipitated out of the organic layer was filtered, washed with water and dried to afford the title compound.

Example 1E 2-(4-methoxyphenyl)benzo[d]thiazole-4-carboxamide

A mixture of EXAMPLE 1D (0.8 g) in polyphosphoric acid (8 mL) was stirred at 100° C. for 3 hours. The mixture was cooled, treated with water and extracted with dichloromethane. The solid that precipitated out of the organic layer was filtered, washed with water and dried to afford the title compound. $^1$H NMR (DMSO-$d_6$) δ 9.24 (s, 1H), 8.33 (d, J=7.9 Hz, 1H), 8.18-8.21 (m, 1H), 8.11-8.14 (m, 2H), 7.94 (s, 1H), 7.56 (t, J=7.9 Hz, 1H), 7.15-7.19 (m, 2H), 3.89 (s, 3H).

Example 1F 2-(4-hydroxyphenyl)benzo[d]thiazole-4-carboxamide

A mixture of EXAMPLE 1E (0.55 g) and a 1M solution of boron tribromide in dichloromethane (25.1 mL) were stirred at ambient temperature for 3 hours. The mixture was poured into 1N hydrochloric acid and extracted with ethyl acetate. The precipitate that formed in the aqueous phase was filtered to afford the title compound. $^1$H NMR (DMSO-$d_6$) δ 10.35 (s, 1H), 9.27 (s, 1H), 8.30 (d, J=6.7 Hz, 1H), 8.17 (d, J=6.7 Hz, 1H), 8.00-8.03 (m, 2H), 8.92 (s, 1H), 7.53 (t, J=7.9 Hz, 1H), 6.95-6.99 (m, 2H).

Example 1G 4-(4-carbamoylbenzo[d]thiazol-2-yl)phenyl trifluoromethanesulfonate

To a solution of EXAMPLE 1F (1.19 g) in N,N-dimethylformamide (24 mL) was added 60% sodium hydride (0.317 g) and N-phenyltrifluoromethanesulfonimide (1.89 g). The mixture was stirred at ambient temperature for 2.5 hours and quenched with water. The precipitate was filtered and dried to afford the title compound. $^1$H NMR (DMSO-$d_6$) δ 9.08 (s, 1H), 8.38-8.44 (m, 3H), 8.23 (dd, J=7.5, 1.6 Hz, 1H), 7.99 (s, 1H), 7.75-7.78 (m, 2H), 7.64 (m, 1H).

Example 2

2-(1,1'-biphenyl-4-yl)-1,3-benzothiazole-4-carboxamide

A mixture of EXAMPLE 1G (25 mg), dichlorobis(triphenylphosphine) palladium(II) (4.36 mg), phenylboronic acid (8.33 mg), 1M sodium carbonate (0.087 mL) and 7:2:3 dimethoxyethane/ethanol/water (1 mL) was heated in a microwave at 160° C. for 10 minutes. The mixture was concentrated and diluted with 1:1 dimethylsulfoxide/methanol. The solid was filtered, dissolved in N,N-dimethylformamide, cooled at 0° C. for 18 hours and filtered to afford the title compound. $^1$H NMR (DMSO-$d_6$) δ 9.24 (d, J=2.1 Hz, 1H), 8.40 (dd, J=7.9, 1.2 Hz, 1H), 8.27 (d, J=8.2 Hz, 2H), 8.23 (dd, J=7.6, 1.2 Hz, 1H), 8.00 (s, 1H), 7.94 (d, J=8.2 Hz, 2H), 7.79 (d, J=7.0 Hz, 2H), 7.62 (t, J=7.8 Hz, 1H), 7.54 (t, J=7.6 Hz, 2H), 7.46 (t, J=7.3 Hz, 1H).

Example 3

2-(4-pyridin-3-ylphenyl)-1,3-benzothiazole-4-carboxamide

The title compound was prepared as described in EXAMPLE 2, substituting pyridin-3-ylboronic acid for phenylboronic acid. Purification by preparative HPLC using a gradient of 10%-100% acetonitrile/water/0.1% trifluoroacetic acid afforded the title compound as the trifluoroacetate salt. $^1$H NMR (DMSO-$d_6$) δ 9.21 (s, 1H), 9.1 (d, J=1.8 Hz, 1H), 8.72 (dd, J=4.9, 1.5 Hz, 1H), 8.38-8.42 (m, 2H), 8.33 (d, J=8.5 Hz, 2H), 8.23 (dd, J=7.6, 1.2 Hz, 1H), 8.04 (d, J=8.5, 2H), 8.00 (d, J=2.1 Hz, 1H), 7.71 (dd, J=7.8, 5.0 Hz, 1H), 7.63 (t, J=7.8 Hz, 1H).

Example 4

2-(4-pyridin-4-ylphenyl)-1,3-benzothiazole-4-carboxamide

The title compound was prepared as described in EXAMPLE 2, substituting pyridin-4-ylboronic acid for phenylboronic acid. The mixture was concentrated and diluted with 1:1 dimethylsulfoxide/methanol. The precipitate was collected to afford the title compound. The filtrate was purified by preparative HPLC using a gradient of 10%-100% acetonitrile/water/0.1% trifluoroacetic acid to provide additional title compound as the trifluoroacetate salt. $^1$H NMR (DMSO-$d_6$) δ 9.20 (s, 1H), 8.72 (d, J=6.1 Hz, 2H), 8.41 (dd, J=7.6, 1.2 Hz, 1H), 8.32 (d, J=8.5 Hz, 2H), 8.23 (dd, J=7.6, 1.2 Hz, 1H), 8.06 (d, J=8.5 Hz, 2H), 8.01 (d, J=1.8 Hz, 1H), 7.82 (d, J=6.1 Hz, 2H), 7.63 (t, J=7.8 Hz, 1H).

Example 5

2-[(2S)-2-methylpyrrolidin-2-yl]-1,3-benzothiazole-4-carboxamide

Example 5A (S)-benzyl 2-(chlorocarbonyl)-2-methylpyrrolidine-1-carboxylate

A solution of (S)-1-(benzyloxycarbonyl)-2-methylpyrrolidine-2-carboxylic acid (1.50 g) in dichloromethane (30 mL) was treated with oxalyl chloride (0.65 mL) and 3 drops of N,N-dimethylformamide at ambient temperature for 1.5 hours. The mixture was concentrated and the crude material used in the next step without further purification.

Example 5B (S)-benzyl 2-(2-bromophenylcarbamoyl)-2-methylpyrrolidine-1-carboxylate To a solution of EXAMPLE 5A in toluene (20 mL) and N,N-dimethylformamide (10 mL) was added 2-bromoaniline (0.891 g) and pyridine (1.38 mL) and the mixture heated at 40° C. for 4 hours. The mixture was treated with ethyl acetate and brine and the organic layer was washed with 5% aqueous citric acid and aqueous sodium bicarbonate, dried over magnesium sulfate, and concentrated to afford the title compound.

Example 5C (S)-benzyl 2-(2-bromophenylcarbamothioyl)-2-methylpyrrolidine-1-carboxylate To a solution of EXAMPLE 5B (1.25 g) in toluene (12 mL) was added Lawesson's reagent (1.212 g) and the mixture heated at reflux for 5 hours. After cooling, the solid was filtered and the filtrate concentrated. The residue was dissolved in ethyl acetate and the solution washed with 5% aqueous citric acid and brine. The organic layer was dried over magnesium sulfate, filtered, and concentrated, and the residue purified by flash chromatography on silica gel using 4:6 to 6:4 dichloromethane/hexane to afford the title compound.

Example 5D (S)-benzyl 2-(4-bromobenzo[d]thiazol-2-yl)-2-methylpyrrolidine-1-carboxylate EXAMPLE 5C (0.60 g) was treated with ethanol (1.8 mL) and stirred with 30% aqueous sodium hydroxide (1.2 mL) for 5 minutes followed by the addition of water (2.4 mL). Aliquots (0.5 mL) of this mixture were added at 1 minute intervals to a solution of potassium ferricyanide (1.823 g) in water (18 mL) at 85° C. The mixture was stirred at 85° C. for 40 minutes and cooled. The mixture was treated with 5% aqueous citric acid and extracted with ethyl acetate. The organic layer was dried over magnesium sulfate, filtered, and concentrated and the residue purified by flash chromatography using 95:5 dichloromethane/ethyl acetate to afford the title compound.

Example 5E (S)-benzyl 2-(4-cyanobenzo[d]thiazol-2-yl)-2-methylpyrrolidine-1-carboxylate A mixture of EXAMPLE 5D (100 mg) and copper(I) cyanide (35.3 mg) in N,N-dimethylformamide (2.5 mL) was heated in a microwave reactor at 205° C. for 30 minutes. This reaction was repeated twice, and after cooling, the combined three reaction mixtures were treated with 5% aqueous citric acid and brine and extracted with ethyl acetate. The aqueous layer was treated with 5% aqueous potassium sodium tartrate and ethyl acetate. The combined organic layers were washed with aqueous sodium bicarbonate, dried over magnesium sulfate, filtered and concentrated, and the residue purified by flash chromatography using 98:2 dichloromethane/ethyl acetate to afford the title compound.

Example 5F

2-[(2S)-2-methylpyrrolidin-2-yl]-1,3-benzothiazole-4-carboxamide

A mixture of EXAMPLE 5E (0.115 g) in polyphosphoric acid (1 mL) was heated at 100° C. for 3.5 hours. After cooling, the residue was treated with water and ethyl acetate. The acidic aqueous layer, which contains the product, was brought to pH=10 with saturated sodium bicarbonate followed by 20% aqueous sodium hydroxide. The cloudy suspension was partially concentrated and the solid material was filtered and washed with water. The solid was purified by reverse-phase HPLC using a gradient of 10%-100% acetonitrile/water/0.1% trifluoroacetic acid to afford the title compound as the trifluoroacetate salt. $^1$H NMR (DMSO-d6) δ 1.87 (s, 3H), 2.07 (m, 1H) 2.22 (m, 1H), 2.35-2.48 (m, 2H), 3.43-3.58 (m, 2H), 7.66 (m, 1H), 7.99 (s br, 1H), 8.25 (dd, J=7.7, 1.2 Hz, 1H), 8.41 (dd, J=8.0, 1.2 Hz, 1H), 8.81 (s br, 1H), 9.63 (s br, 1H), 10.02 (s br, 1H).

G. Compositions

This invention also is directed, in part, to compositions comprising one or more compounds and/or salts of the in invention. The compositions can be pharmaceutical compositions. In some embodiments, the compositions further comprise one or more additional therapeutic agents. Such therapeutic agents can be additional anti-cancer agents.

The preferred composition depends on the method of administration, and typically comprises one or more conventional pharmaceutically acceptable carriers, adjuvants, and/or vehicles (together referred to as "excipients"). Formulation of drugs is generally discussed in, for example, Hoover, J., Remington's Pharmaceutical Sciences (Mack Publishing Co., 1975) and Ansel's Pharmaceutical Dosage Forms and Drug Delivery Systems (Lippincott Williams & Wilkins, 2005).

Solid dosage forms for oral administration include, for example, capsules, tablets, pills, powders, and granules. In such solid dosage forms, the compounds or salts are ordinarily combined with one or more excipients. If administered per os, the compounds or salts can be mixed with, for example, lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in, for example, a dispersion of the compound or salt in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings. Liquid dosage forms for oral administration include, for example, pharmaceutically-acceptable emulsions (including both oil-in-water and water-in-oil emulsions), solutions (including both aqueous and non-aqueous solutions), suspensions (including both aqueous and non-aqueous suspensions), syrups, and elixirs containing inert diluents commonly used in the art (e.g., water). Such compositions also can comprise, for example, wetting, emulsifying, suspending, flavoring (e.g., sweetening), and/or perfuming agents.

Parenteral administration includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the excipients mentioned for use in the formulations for oral administration. A compound or salt of the invention can be dissolved in water, polyethylene glycol, propylene glycol, ethanol, corn oil, cottonseed oil, peanut oil, sesame oil, benzyl alcohol, sodium chloride, and/or various buffers. The pH may be adjusted, if necessary, with a suitable acid, base, or buffer.

Suppositories for rectal administration can be prepared by, for example, mixing a compound or salt of the invention with a suitable nonirritating excipient that is solid at ordinary temperatures, but liquid at the rectal temperature, and will therefore melt in the rectum to release the drug. Suitable excipients include, for example, cocoa butter; synthetic mono-, di-, or triglycerides, fatty acids, and/or polyethylene glycols.

Topical administration includes the use of transdermal administration, such as transdermal patches or iontophoresis devices.

Other excipients and modes of administration known in the pharmaceutical art also may be used.

The preferred total daily dose of the compound or salt (administered in single or divided doses) is typically from about 0.001 to about 100 mg/kg, more preferably from about 0.001 to about 30 mg/kg, and even more preferably from about 0.01 to about 10 mg/kg (i.e., mg of the compound or salt per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the severity of the pathological condition; the route of administration; pharmacological considerations, such as the activity, efficacy, pharmacokinetic, and toxicology profiles of the particular compound or salt used; whether a drug delivery system is utilized; and whether the compound or salt is administered as part of a drug combination. Thus, the dosage regimen actually employed can vary widely, and therefore, can derive from the preferred dosage regimen set forth above.

H. Kits

This invention also is directed, in part, to a kit comprising one or more compounds and/or salts of the in invention. The kit can optionally contain one or more additional therapeutic agents and/or instructions for, for example, using the kit.

I. Methods of Use

As PARP inhibitors, the compounds of this invention have numerous therapeutic applications related to ischemia reperfusion injury, inflammatory diseases, degenerative diseases, protection from adverse effects of cytotoxic compounds, and potentiation of cytotoxic cancer therapy. In particular, compounds of this invention potentiate radiation and chemotherapy by increasing cell death of cancer cells, limiting tumor growth, decreasing metastasis, and prolonging the survival of tumor-bearing mammals. Compounds having formula I can treat leukemia, colon cancer, lung cancer, glioblastomas, lymphomas, melanomas, carcinomas of the breast or prostate, and cervical carcinomas. Compounds having formula I are also expected to be useful when used with alkylating agents, angiogenesis inhibitors, antibodies, antimetabolites, antimitotics, antiproliferatives, aurora kinase inhibitors, Bcr-Abl kinase inhibitors, biologic response modifiers, cyclin-dependent kinase inhibitors, cell cycle inhibitors, cyclooxygenase-2 inhibitors, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, intercalating antibiotics, kinase inhibitors, mammalian target of rapomycin inhibitors, mitogen-activated extracellular signal-regulated kinase inhibitors, non-steroidal anti-inflammatory drugs (NSAID's), platinum chemotherapeutics, polo-like kinase inhibitors, proteasome inhibitors, purine analogs, pyrimidine analogs, receptor tyrosine kinase inhibitors, retinoids/deltoids plant alkaloids, topoisomerase inhibitors and the like.

Alkylating agents include altretamine, AMD-473, AP-5280, apaziquone, bendamustine, brostallicin, busulfan, carboquone, carmustine (BCNU), chlorambucil, Cloretazine™ (VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, treosulfan, trofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs vascular endothelial growth factor receptor tyrosine kinase (VEGFR) inhibitors and the like.

Aurora kinase inhibitors include AZD-1152, MLN-8054, VX-680 and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX™ (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFr immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), Herceptin® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB®, NCS-683664, PU24FC1, PU-3, radicicol, SNX-2112, STA-9090 VER49009 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam) ibuprofin cream, ALEVE® and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin and the like.

Polo-like kinase inhibitors include BI-2536 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™, axitinib (AG-13736), AZD-2171, CP-547,632, IM-862, Macugen (pegaptamib), NEXAVAR® (sorafenib, BAY43-9006), pazopanib (GW-786034), (PTK-787, ZK-222584), SUTENT® (sunitinib, SU-11248), VEGF trap, vatalanib, ZACTIMA™ (vandetanib, ZD-6474) and the like.

Antimetabolites include ALIMTA® (premetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR, enocitabine, ethnylcytidine, fludarabine, hydroxyurea, 5-fluorouracil (5-FU) alone or in combination with leucovorin, GEMZAR® (gemcitabine), hydroxyurea, ALKERAN® (melphalan), mercaptopurine, 6-mercaptopurine riboside, methotrexate, mycophenolic acid, nelarabine, nolatrexed, ocfosate, pelitrexol, pentostatin, raltitrexed, Ribavirin, triapine, trimetrexate, S-1, tiazofurin, tegafur, TS-1, vidarabine, UFT and the like.

Antibiotics include intercalating antibiotics aclarubicin, actinomycin D, amrubicin, annamycin, adriamycin, BLENOXANE® (bleomycin), daunorubicin, CAELYX® or MYOCET® (doxorubicin), elsamitrucin, epirbucin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL®, (flutamide), EVISTA® (raloxifene), fadrozole, FARESTON® (toremifene), FASLODEX® (fulvestrant), FEMARA®, (letrozole), formestane, glucocorticoids, HECTOROL® or RENAGEL® (doxercalciferol), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), predisone, PROPECIA® (finasteride), rilostane, SUPREFACT® (buserelin), TRELSTAR® (luteinizing hormone releasing hormone (LHRH)), vantas, VETORYL®, (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN (liposomal tretinoin), TARGRETIN® (bexarotene), LGD-1550 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b), or interferon gamma-n1, combinations thereof and the like. Other agents include ALFAFERONE®, BAM-002, BEROMUN® (tasonermin), BEXXAR® (tositumomab), CamPath® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010, melanoma vaccine, mitumomab, molgramostim, MYLOTARG™ (gemtuzumab ozogamicin), NEUPOGEN® (filgrastim), OncoVAC-CL, OvaRex® (oregovomab), pemtumomab (Y-muHMFG1), PROVENGE®, sargaramostim, sizofilan, teceleukin, TheraCys®, ubenimex, VIRULIZIN®, Z-100, WF-10, PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth, or differentiation of tissue cells to direct them to have anti-tumor activity and include krestin, lentinan, sizofuran, picibanil PF-3512676 (CpG-8954), ubenimex and the like.

Pyrimidine analogs include cytarabine (ara C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881, vinflunine, ZK-EPO and the like.

Compounds of the present invention are also intended to be used as a radiosensitizer that enhances the efficacy of radiotherapy. Examples of radiotherapy include, but are not limited to, external beam radiotherapy, teletherapy, brachtherapy and sealed and unsealed source radiotherapy.

Additionally, compounds having formula I may be combined with other chemptherapeutic agents such as ABRAXANE™ (ABI-007), ABT-100 (farnesyl transferase inhibitor), ADVEXIN®, ALTOCOR® or MEVACOR® (lovastatin), AMPLIGEN® (poly I:poly C12U, a synthetic RNA), APTOSYN™ (exisulind), AREDIA® (pamidronic acid), arglabin, L-asparaginase, atamestane (1-methyl-3,17-dione-androsta-1,4-diene), AVAGE® (tazarotne), AVE-8062, BEC2 (mitumomab), cachectin or cachexin (tumor necrosis factor), canvaxin (vaccine), CeaVac™ (cancer vaccine), CELEUK® (celmoleukin), CEPLENE® (histamine dihydrochloride), CERVARIX™ (human papillomavirus vaccine), CHOP® (C: CYTOXAN® (cyclophosphamide); H: ADRIAMYCIN® (hydroxydoxorubicin); O: Vincristine (ONCOVIN®; P: prednisone), CyPat™, combrestatin A4P, DAB(389)EGF or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906, GARDASIL® (quadrivalent human papillomavirus (Types 6, 11, 16, 18) recombinant vaccine), gastrimmune, genasense, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), OncoVAX (IL-2 Vaccine), ORATHECIN™ (rubitecan), OSIDEM® (antibody-based cell drug), OvaRex® MAb (murine monoclonal antibody), paditaxel, PANDIMEX™ (aglycone saponins from ginseng comprising 20(S)protopanaxadiol (aPPD) and 20(S)protopanaxatriol (aPPT)), panitumumab, PANVAC-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces staurospores*), talabostat (PT100), TARGRETIN® (bexarotene), Taxoprexin® (DHA-paclitaxel), TELCYTA™ (TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio) quinazoline dihydrochloride), TNFerade™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS™ (trabectedin), ZD-6126, ZINECARD® (dexrazoxane), zometa (zolendronic acid), zorubicin and the like.

In one embodiment, compounds having Formula I are used in a method of treating cancer in a mammal comprising administering thereto a therapeutically acceptable amount of a compound of Formula I in combination with a chemotherapeutic agent selected from temozolomide, dacarbazine, cyclophosphamide, carmustine, melphalan, lomustine, carboplatin, cisplatin, 5-FU+/−leucovorin, gemcitabine, methotrexate, bleomycin, irinotecan, camptothecin, or topotecan.

It is expected that compounds having Formula I would also inhibit growth of cells derived from a pediatric cancer or neoplasm including embryonal rhabdomyosarcoma, pediatric acute lymphoblastic leukemia, pediatric acute myelogenous leukemia, pediatric alveolar rhabdomyosarcoma, pediatric anaplastic ependymoma, pediatric anaplastic large cell lymphoma, pediatric anaplastic medulloblastoma, pediatric atypical teratoid/rhabdoid tumor of the central nervous syatem, pediatric biphenotypic acute leukemia, pediatric Burkitts lymphoma, pediatric cancers of Ewing's family of tumors such as primitive neuroectodermal rumors, pediatric diffuse anaplastic Wilm's tumor, pediatric favorable histology Wilm's tumor, pediatric glioblastoma, pediatric medulloblastoma, pediatric neuroblastoma, pediatric neuroblastoma-derived myelocytomatosis, pediatric pre-B-cell cancers (such as leukemia), pediatric psteosarcoma, pediatric rhabdoid kidney tumor, pediatric rhabdomyosarcoma, and pediatric T-cell cancers such as lymphoma and skin cancer and the like (commonly-owned U.S. application Ser. No. 10/988,338, Cancer Res., 2000, 60, 6101-10); and autoimmune disorders include, acquired immunodeficiency disease syndrome, autoimmune lymphoproliferative syndrome, hemolytic anemia, inflammatory diseases, thrombocytopenia and the like (Current Allergy and Asthma Reports 2003, 3:378-384; Br. J. Haematol. 2000 September; 110(3): 584-90; Blood 2000 Feb. 15; 95(4):1283-92; and New England Journal of Medicine 2004 September; 351(14): 1409-1418).

TABLE 1

Inhibition of PARP by Compounds Having Formula I

| Example | PARP-1 ($K_i$, nM) |
| --- | --- |
| 1 | 45 |
| 2 | 316 |
| 3 | 9.5 |
| 4 | 26 |

Cellular PARP Assay:

The cellular assay measures the formation of poly ADP-ribose by PARP within cells and demonstrates that compounds penetrate cell membranes and inhibit PARP in intact cells. C41 cells are treated with a compound of this invention for 30 minutes in 96 well plate. PARP is then activated by damaging DNA with 1 mM $H_2O_2$ for 10 minutes. The cells are then washed with ice-cold PBS once and fixed with pre-chilled methanol:acetone (7:3) at −20° C. for 10 minutes. After air-drying, the plates are rehydrated with PBS and blocked 5% non-fat dry milk in PBS-TWEEN20® (Sigma, St. Louis, Mo.) (0.05%) (blocking solution) for 30 minutes at room temperature. The cells are incubated with anti-PAR antibody 10H (1:50) in Blocking solution at 37° C. for 60 minutes followed by washing with PBS-TWEEN20® 5 times, and incubation with goat anti-mouse fluorescein 5(6)-isothiocyanate-coupled antibody (1:50) and 1 μg/ml 4',6-diamidino-2-phenylindole (DAPI) in blocking solution at 37° C. for 60 minutes. After washing with PBS-TWEEN20® 5 times, the analysis is performed using an FMAX FLUORESCENCE MICROPLATE READER® (Molecular Devices, Sunnyvale, Calif.), set at the excitation wavelength of 490 nm and emission wavelength of 528 nm fluorescein 5(6)-isothiocyanate (FITC) or the excitation wavelength of 355 nm and emission wavelength of 460 nm (DAPI). The PARP activity (FITC signal) is normalized with cell numbers (DAPI).

The invention claimed is:

1. A compound having a structure of Formula I

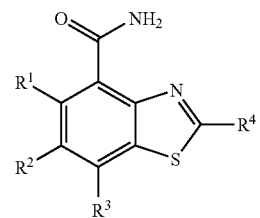

(I)
wherein
$R^1$ is selected from the group consisting of hydrogen, halogen and $C_1$ to $C_3$ alkyl;
$R^2$ is selected from the group consisting of hydrogen, halogen and $C_1$ to $C_3$ alkyl;
$R^3$ is selected from the group consisting of hydrogen, halogen and $C_1$ to $C_3$ alkyl;
$R^4$ is selected from the group consisting of alkyl, alkenyl, alkynyl, cycloalkyl, cycloalkenyl, and aryl wherein (a) the $R^4$ alkyl, alkenyl, alkynyl substituents are optionally substituted with one or more substituents selected from the group consisting of $R^6$, halogen, cyano, oxo, —$OR^{10}$, —$C(O)R^{10}$, —$C(O)OR^{10}$, —$OC(O)R^{10}$, —$NR^{11}R^{12}$, —$NR^{11}C(O)R^{12}$, —$NHC(O)NHR^{11}$, —$C(O)NR^{11}R^{12}$, —$SR^{10}$, —$S(O)R^{10}$, —$SO_2R^{10}$, —$OC(O)OR^{10}$, —$SO_2NR^{11}R^{12}$, —$N_3$, —$NO_2$, —$CF_3$, —$CF_2CF_3$, —$OCF_3$, and —$OCF_2CF_3$; (b) wherein the $R^4$ cycloalkyl, cycloalkenyl, and aryl substituents are optionally substituted with one or more $R^5$;
$R^5$ is selected from the group consisting of $R^6$, alkyl, alkenyl, alkynyl, halogen, cyano, oxo, —$OR^{13}$, —$C(O)R^{13}$, —$C(O)OR^{13}$, —$OC(O)R^{13}$, —$NR^{14}NR^{15}$, —$NHC(O)NHR^{14}$, —$C(O)NR^{14}R^{15}$, —$SR^{13}$, —$S(O)R^{13}$, —$OC(O)OR^{13}$, —$SO_2NR^{14}R^{15}$, —$N_3$, —$NO_2$, —$CF_3$, —$CF_2CF_3$, —$OCF_3$, and —$OCF_2CF_3$ wherein the $R^5$ alkyl, alkenyl, and alkynyl substituents are optionally substituted with one or more substituents selected from the group consisting of aryl, heterocyclyl, cycloalkyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{13}$ and —$C(O)NR^{14}R^{15}$;
$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —$OR^{16}$, —$C(O)R^{16}$, —$C(O)OR^{16}$, —$OC(O)R^{16}$, —$NR^{17}R^{18}$, —$NR^{17}C(O)R^{18}$, —$NHC(O)NHR^{17}$, —$C(O)NR^{17}R^{18}$, $SR^{16}$, $S(O)R^{16}$, $SO_2R^{16}$, $OC(O)OR^{16}$, $SO_2NR^{17}R^{18}$, —$N_3$, —$NO_2$, —$CF_3$, —$CF_2CF_3$, —$OCF_3$, and —$OCF_2CF_3$;
$R^{10}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{11}$ and $R^{12}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

or a pharmaceutically acceptable salt thereof.

2. A compound having a structure of the Formula II

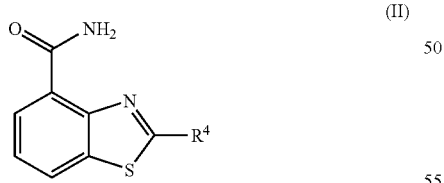

wherein:

$R^4$ is selected from the group consisting of alkyl, alkenyl, alkynyl, cycloalkyl, cycloalkenyl, and aryl wherein (a) the $R^4$ alkyl, alkenyl, and alkynyl substituents are optionally substituted with $R^6$ and further unsubstituted or substituted with one or more substituents selected from the group consisting of alkyl, alkenyl, alkynyl, halogen, cyano, oxo, —OR$^{10}$, —C(O)R$^{10}$, —C(O)OR$^{10}$, —OC(O)R$^{10}$, —NR$^{11}$R$^{12}$, —NR$^{11}$C(O)R$^{12}$, —NHC(O)NHR$^{11}$, —C(O)NR$^{11}$R$^{12}$, —SR$^{10}$, —S(O)R$^{10}$, —SO$_2$R$^{10}$, —OC(O)OR$^{10}$, —SO$_2$NR$^{11}$R$^{12}$, —N$_3$, —NO$_2$, —CF$_3$, —CF$_2$CF$_3$, —OCF$_3$, and —OCF$_2$CF$_3$ (b) wherein the $R^4$ cycloalkyl, cycloalkenyl, and aryl substituents are optionally substituted with one or more $R^5$;

$R^5$ is selected from the group consisting of $R^6$, alkyl, alkenyl, alkynyl, halogen, cyano, oxo, —OR$^{13}$, —C(O)R$^{13}$, —C(O)OR$^{13}$, —OC(O)R$^{13}$, —NR$^{14}$NR$^{15}$, —NHC(O)NHR$^{14}$, —C(O)NR$^{14}$R$^{15}$, —SR$^{13}$, —S(O)R$^{13}$, —OS(O)$_2$CF$_3$, —SO$_2$R$^{13}$, —OC(O)OR$^{13}$, —SO$_2$NR$^{14}$R$^{15}$, —N$_3$, —NO$_2$, —CF$_3$, —CF$_2$CF$_3$, —OCF$_3$, and —OCF$_2$CF$_3$ wherein the $R^5$ alkyl, alkenyl, and alkynyl substituents are optionally substituted with one or more substituents selected from the group consisting of aryl, heterocyclyl, cycloalkyl, halogen, cyano, oxo, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{13}$ and —C(O)NR$^{14}$R$^{15}$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —OR$^{16}$, —C(O)R$^{16}$, —C(O)OR$^{16}$, —OC(O)R$^{16}$, —NR$^{17}$R$^{18}$, —NR$^{17}$C(O)R$^{18}$, —NHC(O)NHR$^{17}$, —C(O)NR$^{17}$R$^{18}$, SR$^{16}$, S(O)R$^{16}$, SO$_2$R$^{16}$, OC(O)OR$^{16}$, SO$_2$NR$^{17}$R$^{18}$, —N$_3$, —NO$_2$, —CF$_3$, —CF$_2$CF$_3$, —OCF$_3$, and —OCF$_2$CF$_3$;

$R^{10}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{11}$ and $R^{12}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo or a pharmaceutically acceptable salt thereof.

3. The compound of claim 2 wherein $R^4$ is selected from the group consisting of alkyl, cycloalkyl, cycloalkenyl, and aryl; or a pharmaceutically acceptable salt thereof.

4. The compound of claim 2, wherein $R^4$ is phenyl.

5. The compound of claim 4 wherein $R^4$ is optionally substituted with one to three $R^5$, wherein $R^5$ is selected from the group consisting of $R^6$, unsubstituted alkyl, and —OS$(O)_2$CF$_3$, wherein $R^6$ is unsubstituted phenyl or an unsubstituted heterocyclyl selected from the group consisting of

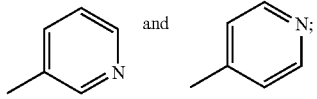

or a pharmaceutically acceptable salt thereof.

6. A compound having a structure of the Formula III

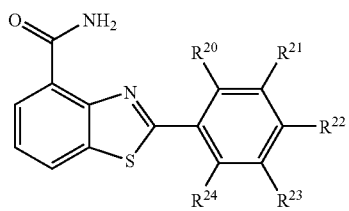

(III)

wherein $R^{20}$, $R^{21}$, $R^{22}$, $R^{23}$ and $R^{24}$ are independently selected from the group consisting of hydrogen, $R^6$, alkyl, alkenyl, alkynyl, halogen, cyano, oxo, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{14}$, —C(O)NR$^{14}$R$^{15}$, —SR$^{13}$, —S(O)R$^{13}$, —OS(O)$_2$CF$_3$, —SO$_2$R$^{13}$, —OC(O)OR$^{13}$, —SO$_2$NR$^{14}$R$^{15}$, —N$_3$, —NO$_2$, —CF$_3$, —CF$_2$CF$_3$, —OCF$_3$, and —OCF$_2$CF$_3$;

$R^6$ is aryl or heterocyclyl wherein the $R^6$ aryl and heterocyclyl substituents are optionally substituted with one or more substituents independently selected from the group consisting of alkyl, alkenyl, alkynyl, aminoalkyl, halogen, cyano, oxo, —OR$^{16}$, —C(O)R$^{16}$, —C(O)OR$^{16}$, —OC(O)R$^{16}$, —NR$^{17}$R$^{18}$, —NR$^{17}$C(O)R$^{18}$, —NHC(O)NHR$^{17}$, —C(O)NR$^{17}$R$^{18}$, SR$^{16}$, S(O)R$^{16}$, SO$_2$R$^{16}$, OC(O)OR$^{16}$, SO$_2$NR$^{17}$R$^{18}$, —N$_3$, —NO$_2$, —CF$_3$, —CF$_2$CF$_3$, —OCF$_3$, and —OCF$_2$CF$_3$;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

or a pharmaceutically acceptable salt thereof.

7. The compound of claim 6 wherein at least 2 of $R^{20}$, $R^{21}$, $R^{23}$ and $R^{24}$ are hydrogen, and $R^{22}$ is selected from the group consisting of $R^6$, alkyl, —OR$^{13}$, —C(O)R$^{13}$, —C(O)OR$^{13}$, —OC(O)R$^{13}$, —NR$^{14}$R$^{15}$, —NR$^{14}$C(O)R$^{15}$, —NHC(O)NHR$^{14}$, —C(O)NR$^{14}$R$^{15}$, —SR$^{13}$, —S(O)R$^{13}$, —OS(O)$_2$CF$_3$, —SO$_2$R$^{13}$, —OC(O)OR$^{13}$, —SO$_2$NR$^{14}$R$^{15}$, —N$_3$, —NO$_2$, —CF$_3$, —CF$_2$CF$_3$, —OCF$_3$, and —OCF$_2$CF$_3$ $R^6$ is phenyl or 5, 6 or 7-membered heterocyclyl, wherein the $R^6$ phenyl and heterocyclyl substituents are optionally substituted with one or more substituents independently selected from the group consisting of alkyl, alkenyl, aminoalkyl, halogen, oxo, —OR$^{16}$, —C(O)R$^{16}$, —C(O)OR$^{16}$, —NR$^{17}$R$^{18}$, —NR$^{17}$C(O)R$^{18}$, —C(O)NR$^{17}$R$^{18}$, SR$^{16}$, S(O)R$^{16}$, SO$_2$R$^{16}$, SO$_2$NR$^{17}$R$^{18}$, —CF$_3$, and OCF$_3$;

$R^{13}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo;

$R^{14}$ and $R^{15}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

$R^{16}$, at each occurrence, is independently selected from the group consisting of hydrogen, alkyl, alkenyl, alkynyl, aryl, heterocyclyl, and cycloalkyl, wherein the alkyl, alkenyl, alkynyl, aryl, heterocyclyl, and cycloalkyl are optionally substituted with one or more substituents independently selected from the group consisting of aryl, heterocyclyl, cycloalkyl, hydroxyl, halogen, cyano, and oxo; and $R^{17}$ and $R^{18}$, at each occurrence, are independently selected from the group consisting of hydrogen, alkyl, alkenyl, alkynyl, aryl, heterocyclyl, cycloalkenyl, and cycloalkyl, wherein the alkyl, alkenyl, alkynyl, heterocyclyl, and cycloalkyl are optionally substituted with one or more substituents independently selected from the group consisting of aryl, heterocyclyl, cycloalkyl, hydroxyl, halogen, cyano, and oxo;

or a pharmaceutically acceptable salt thereof.

8. The compound of claim 6 wherein $R^{20}$, $R^{21}$, $R^{23}$ and $R^{24}$ are hydrogen, and $R^{22}$ is selected from the group consisting of $R^6$, alkyl, alkenyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{14}$, —$C(O)NR^{14}R^{15}$, —$SR^{13}$, —$S(O)R^{13}$, —$OS(O)_2CF_3$, —$SO_2R^{13}$, —$OC(O)OR^{13}$, —$SO_2NR^{14}R^{15}$, —$N_3$, —$NO_2$, —$CF_3$, —$CF_2CF_3$, —$OCF_3$, and —$OCF_2CF_3$ wherein the $R^{22}$ alkyl, alkenyl, and alkynyl substituents are optionally substituted with one or more substituents selected from the group consisting of aryl, heterocyclyl, cycloalkyl, halogen, cyano, oxo, —$OR^{13}$, —$C(O)R^{13}$, —$C(O)OR^{13}$, —$OC(O)R^{13}$, —$NR^{14}R^{15}$, —$NR^{14}C(O)R^{15}$, —$NHC(O)NHR^{13}$ and —$C(O)NR^{14}R^{15}$;

$R^6$ is aryl or 3, 4, 5, 6, 7 or 8 membered ring heterocyclyl wherein the $R^6$ aryl and heterocyclyl substituents are optionally substituted with one or more substituents independently selected from the group consisting of alkyl, alkenyl, halogen, cyano, oxo, —$OR^{16}$, —$C(O)R^{16}$, —$C(O)OR^{16}$, —$OC(O)R^{16}$, —$NR^{17}R^{18}$, —$NR^{17}C(O)R^{18}$, —$C(O)NR^{17}R^{18}$, $SR^{16}$, $S(O)R^{16}$, $SO_2R^{16}$, $SO_2NR^{17}R^{18}$, —$CF_3$, —$CF_2CF_3$, and —$OCF_3$;

$R^{10}$, at each occurrence, is independently selected from the group consisting of hydrogen and alkyl;

$R^{11}$ and $R^{12}$, at each occurrence, are independently selected from the group consisting of hydrogen and alkyl;

$R^{13}$, at each occurrence, is independently selected from the group consisting of hydrogen and alkyl;

$R^{14}$ and $R^{15}$, at each occurrence, are independently selected from the group consisting of hydrogen and alkyl;

$R^{16}$, at each occurrence, is independently selected from the group consisting of hydrogen and alkyl; and $R^{17}$ and $R^{18}$, at each occurrence, are independently selected from the group consisting of hydrogen and alkyl;

or a pharmaceutically acceptable salt thereof.

9. The compound of claim 6 wherein $R^{22}$ is selected from the group consisting of $R^6$, alkyl, —$OR^{13}$, and —$OS(O)_2CF_3$;

$R^6$ is unsubstituted phenyl or an unsubstituted heterocyclyl selected from the group consisting of

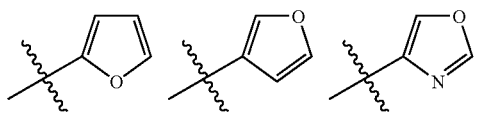

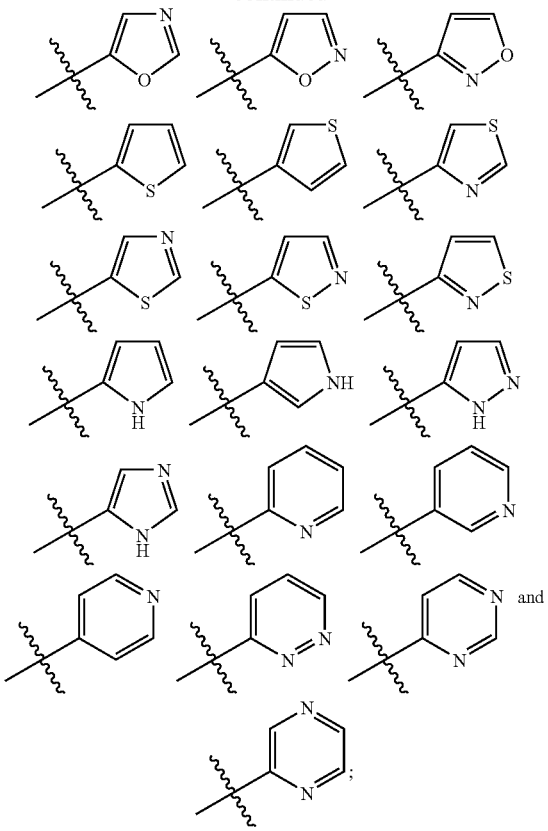

and wherein $R^{13}$ is selected from the group consisting of hydrogen and alkyl;

or a pharmaceutically acceptable salt thereof.

10. A compound selected from the group consisting of

4-[4-(aminocarbonyl)-1,3-benzothiazol-2-yl]phenyl trifluoromethanesulfonate;

2-(1,1'-biphenyl-4-yl)-1,3-benzothiazole-4-carboxamide;

2-(4-pyridin-3-ylphenyl)-1,3-benzothiazole-4-carboxamide; and 2-(4-pyridin-4-ylphenyl)-1,3-benzothiazole-4-carboxamide;

or a pharmaceutically acceptable salt thereof.

11. A pharmaceutical composition comprising a compound or pharmaceutically acceptable salt of claim 1 and pharmaceutically acceptable excipient.

* * * * *

UNITED STATES PATENT AND TRADEMARK OFFICE
CERTIFICATE OF CORRECTION

| | |
|---|---|
| PATENT NO. | : 8,093,396 B2 |
| APPLICATION NO. | : 12/689290 |
| DATED | : January 10, 2012 |
| INVENTOR(S) | : Przytulinska et al. |

Page 1 of 1

It is certified that error appears in the above-identified patent and that said Letters Patent is hereby corrected as shown below:

On the Title page, Item (54) and Col. 1, line 1, title: "BENZTHIAZOLE" to read as --BENZOTHIAZOLE--

Column 36, line 31, claim 1: "aryl wherein" to read as --aryl, wherein--

Column 36, line 39, claim 1: "—$OCF_2CF_3$; (b) wherein" to read as -- —$OCF_2CF_3$; and (b)--

Column 36, line 44, claim 1: "—$NR^{14}NR^{15}$," to read as -- —$NR^{14}R^{15}$, —$NR^{14}C(O)R^{15}$,--

Column 36, line 45, claim 1: "—$S(O)R^{13}$," to read as -- —$S(O)R^{13}$, —$OS(O)_2CF_3$, —$SO_2R^{13}$,--

Column 36, line 47, claim 1: "—$OCF_2CF_3$" to read as -- —$OCF_2CF_3$,--

Column 36, line 54, claim 1: "heterocyclyl wherein" to read as --heterocyclyl, wherein--

Column 37, line 46, claim 2: "the Formula" to read as --Formula--

Column 37, line 59, claim 2: "aryl wherein" to read as --aryl, wherein--

Column 38, line 01, claim 2: "—$OCF_2CF_3$ (b) wherein" to read as -- —$OCF_2CF_3$; and (b)--

Column 38, line 07, claim 2: "—$NR^{14}NR^{15}$," to read as -- —$NR^{14}R^{15}$, —$NR^{14}C(O)R^{15}$,--

Column 38, line 11, claim 2: "—$OCF_2CF_3$" to read as -- —$OCF_2CF_3$,--

Column 38, line 19, claim 2: "heterocyclyl wherein" to read as --heterocyclyl, wherein--

Column 39, line 08, claim 2: "oxo" to read as --oxo;--

Column 39, line 28, claim 6: "the Formula" to read as --Formula--

Column 39, line 47, claim 6: "heterocyclyl wherein" to read as --heterocyclyl, wherein--

Column 40, line 29, claim 7: "—$OCF_2CF_3$" to read as -- —$OCF_2CF_3$;--

Column 41, line 12, claim 8: "—$OCF_2CF_3$" to read as -- —$OCF_2CF_3$,--

Column 41, line 19, claim 8: "heterocyclyl wherein" to read as --heterocyclyl, wherein--

Signed and Sealed this
Fourth Day of December, 2012

David J. Kappos
*Director of the United States Patent and Trademark Office*